United States Patent
Bradley et al.

(10) Patent No.: US 8,173,807 B2
(45) Date of Patent: May 8, 2012

(54) PYRIDINE, PYRIMIDINE AND PYRAZINE DERIVATIVES AS GPCR AGONISTS

(75) Inventors: Stuart Edward Bradley, Oxford (GB); Matthew Colin Thor Fyfe, Oxford (GB); Gerard Hugh Thomas, Oxford (GB)

(73) Assignee: Prosidion Limited, Oxford (GB)

( * ) Notice: Subject to any disclaimer, the term of this patent is extended or adjusted under 35 U.S.C. 154(b) by 614 days.

(21) Appl. No.: 11/794,641

(22) PCT Filed: Dec. 30, 2005

(86) PCT No.: PCT/GB2005/050266
§ 371 (c)(1),
(2), (4) Date: Oct. 12, 2009

(87) PCT Pub. No.: WO2006/070208
PCT Pub. Date: Jul. 6, 2006

(65) Prior Publication Data
US 2010/0035897 A1     Feb. 11, 2010

(30) Foreign Application Priority Data
Dec. 31, 2004   (GB) .................................. 0428514.4

(51) Int. Cl.
A61K 31/506    (2006.01)
A61K 31/4545   (2006.01)
C07D 401/14    (2006.01)
A61P 3/00      (2006.01)
A61P 3/04      (2006.01)
A61P 3/10      (2006.01)

(52) U.S. Cl. ........ 544/328; 544/333; 546/193; 514/256; 514/318

(58) Field of Classification Search .................. 544/328, 544/333; 546/193; 514/256, 318
See application file for complete search history.

(56) References Cited

U.S. PATENT DOCUMENTS
5,629,325 A * 5/1997 Lin et al. ....................... 514/318

FOREIGN PATENT DOCUMENTS
| WO | WO-02068387 | 9/2002 |
| WO | WO-02068388 | 9/2002 |
| WO | WO 03/27100 * | 4/2003 |
| WO | WO-03068236 A1 | 8/2003 |
| WO | WO-2005061489 A1 | 7/2005 |

OTHER PUBLICATIONS

Fujita et al. in Tetrahedron Letters vol. 36, pp. 5247-5250 (1995).*
Fyfe et al. in Annual Reports in Medicinal Chemistry, vol. 42, pp. 129-145.*
J. G. Cannon Chapter Nineteen in Burger's Medicinal Chemistry and Drug Discovery, Fifth Edition, vol. I: Principles and Practice, Wiley-Interscience 1995, pp. 783-802, 784.*
Schafer et al. Drug Discovery Today 2008, 13 (21/22), 913-916.*
Overton et al. in British Journal of Pharmacology (2008) 153, S76-S81.*
Jones et al. in Expert Opinion on Therapeutic Patents (2009) 19 (10), 1339-1359.*
Borgstrom et al. "Electron Donor-Accepted Dyads and Triads Based on Tris(bipyridine)ruthenium(II) and Benzoquinone: Synthesis, Characterization, and Photoinduced Electron Transfer Reactions." *Inorg. Chem.* 42(2003):5173-5184.

* cited by examiner

*Primary Examiner* — Timothy Thomas
*Assistant Examiner* — Dennis Heyer
(74) *Attorney, Agent, or Firm* — Mintz, Levin, Cohn, Ferris, Glovsky and Popeo, P.C.; Ivor R. Elrifi; Heidi A. Erlacher

(57) ABSTRACT

Compounds of formula (I): $R^1$-A-V—B—$R^2$, wherein V is phenyl or a 6-membered heteroaryl ring containing up to three N-atoms, or pharmaceutically acceptable salts thereof, are agonists of GPR116 and are useful for the treatment of obesity, and for the treatment of diabetes.

17 Claims, No Drawings

PYRIDINE, PYRIMIDINE AND PYRAZINE DERIVATIVES AS GPCR AGONISTS

BACKGROUND OF THE INVENTION

The present invention is directed to G-protein coupled receptor (GPCR) agonists. In particular, the present invention is directed to agonists of GPR116 that are useful for the treatment of obesity, e.g. as regulators of satiety, and for the treatment of diabetes.

Obesity is characterized by an excessive adipose tissue mass relative to body size. Clinically, body fat mass is estimated by the body mass index (BMI; weight(kg)/height(m)$^2$), or waist circumference. Individuals are considered obese when the BMI is greater than 30 and there are established medical consequences of being overweight. It has been an accepted medical view for some time that an increased body weight, especially as a result of abdominal body fat, is associated with an increased risk for diabetes, hypertension, heart disease, and numerous other health complications, such as arthritis, stroke, gallbladder disease, muscular and respiratory problems, back pain and even certain cancers.

Pharmacological approaches to the treatment of obesity have been mainly concerned with reducing fat mass by altering the balance between energy intake and expenditure. Many studies have clearly established the link between adiposity and the brain circuitry involved in the regulation of energy homeostasis. Direct and indirect evidence suggest that serotonergic, dopaminergic, adrenergic, cholinergic, endocannabinoid, opioid, and histaminergic pathways in addition to many neuropeptide pathways (e.g. neuropeptide Y and melanocortins) are implicated in the central control of energy intake and expenditure. Hypothalamic centres are also able to sense peripheral hormones involved in the maintenance of body weight and degree of adiposity, such as insulin and leptin, and fat tissue derived peptides.

Drugs aimed at the pathophysiology associated with insulin dependent Type I diabetes and non-insulin dependent Type II diabetes have many potential side effects and do not adequately address the dyslipidaemia and hyperglycaemia in a high proportion of patients. Treatment is often focused at individual patient needs using diet, exercise, hypoglycemic agents and insulin, but there is a continuing need for novel antidiabetic agents, particularly ones that may be better tolerated with fewer adverse effects.

Similarly, metabolic syndrome (syndrome X) which is characterized by hypertension and its associated pathologies including atherosclerosis, lipidemia, hyperlipidemia and hypercholesterolemia have been associated with decreased insulin sensitivity which can lead to abnormal blood sugar levels when challenged. Myocardial ischemia and microvascular disease is an established morbidity associated with untreated or poorly controlled metabolic syndrome.

There is a continuing need for novel antiobesity and antidiabetic agents, particularly ones that are well tolerated with few adverse effects.

GPR116 is a GPCR identified as SNORF25 in WO00/50562 which discloses both the human and rat receptors, U.S. Pat. No. 6,468,756 also discloses the mouse receptor (accession numbers: AAN95194 (human), AAN95195 (rat) and ANN95196 (mouse)).

In humans, GPR116 is expressed in the pancreas, small intestine, colon and adipose tissue. The expression profile of the human GPR116 receptor indicates its potential utility as a target for the treatment of obesity and diabetes.

International patent application WO2005/061489 (published after the priority date of the present application) discloses heterocyclic derivatives as GPR116 receptor agonists.

International patent application WO03/068236 discloses the compounds tert-butyl 4-(3-pyridin-4-ylbenzyl)piperidine-1-carboxylate and 4-(3-pyridin-4-ylbenzyl)piperidine as intermediates for the synthesis of 5HT-1 receptor modulators, no pharmaceutical utility is suggested for these compounds.

The present invention relates to agonists of GPR116 which are useful for the treatment of obesity, e.g. as regulators of satiety, and for the treatment of diabetes.

SUMMARY OF THE INVENTION

Compounds of formula (I):

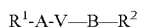

or pharmaceutically acceptable salts thereof, are agonists of GPR116 and are useful for the prophylactic or therapeutic treatment of obesity, and for the treatment of diabetes.

DETAILED DESCRIPTION OF THE INVENTION

The present invention is directed to a compound of formula (I), or a pharmaceutically acceptable salt thereof:

wherein V is phenyl or a 6-membered heteroaryl ring containing up to three N atoms;

A is —CH=CH— or $(CH_2)_n$;

B is —CH=CH— or $(CH_2)_n$, where one of the $CH_2$ groups may be replaced by O, $NR^5$, $S(O)_m$, $C(O)$ or $C(O)NR^{12}$;

n is independently 0, 1, 2 or 3;

m is independently 0, 1 or 2;

$R^1$ is 3- or 4-pyridyl, 4- or 5-pyrimidinyl or 2-pyrazinyl, any of which may be optionally substituted by one or more substituents selected from halo, $C_{1-4}$ alkyl, $C_{1-4}$ fluoroalkyl, $C_{2-4}$ alkenyl, $C_{2-4}$ alkynyl, $C_{3-7}$ cycloalkyl, aryl, $OR^6$, CN, $NO_2$, $S(O)_mR^6$, $CON(R^6)_2$, $N(R^6)_2$, $NR^{10}COR^6$, $NR^{10}SO_2R^6$, $SO_2N(R^6)_2$, a 4- to 7-membered heterocyclyl group or a 5- or 6-membered heteroaryl group;

$R^2$ is 4- to 7-membered cycloalkyl substituted by $R^3$, $C(O)OR^3$, $C(O)R^3$ or $S(O)_2R^3$, or 4- to 7-membered heterocyclyl, containing one or two nitrogen atoms which is unsubstituted or substituted by $C(O)OR^4$, $C(O)R^3$, $S(O)_2R^3$, $C(O)NHR^4$, $P(O)(OR^{11})_2$ or a 5- or 6-membered nitrogen containing heteroaryl group;

$R^3$ is $C_{3-8}$ alkyl, $C_{3-8}$ alkenyl or $C_{3-8}$ alkynyl, any of which may be optionally substituted with up to 5 fluoro or chloro atoms, and may contain a $CH_2$ group that may be replaced by O, or $C_{3-7}$ cycloalkyl, aryl, heterocyclyl, heteroaryl, $C_{1-4}$ alkyl$C_{3-7}$cycloalkyl, $C_{1-4}$ alkylaryl, $C_{1-4}$ alkylheterocyclyl or $C_{1-4}$ alkylheteroaryl, any of which may be optionally substituted with one or more substituents selected from halo, $C_{1-4}$ alkyl, $C_{1-4}$ fluoroalkyl, $OR^6$, CN, $CO_2C_{1-4}$ alkyl, $N(R^6)_2$ and $NO_2$;

$R^4$ is $C_{2-8}$ alkyl, $C_{2-8}$ alkenyl or $C_{2-8}$ alkynyl, any of which may be optionally substituted with up to 5 fluoro or chloro atoms, and may contain a $CH_2$ group that may be replaced by O, or $C_{3-7}$ cycloalkyl, aryl, heterocyclyl, heteroaryl, $C_{1-4}$ alkyl$C_{3-7}$cycloalkyl, $C_{1-4}$ alkylaryl, $C_{1-4}$ alkylheterocyclyl or $C_{1-4}$ alkylheteroaryl, any of which may be substituted with one or more substituents selected from halo, $C_{1-4}$ alkyl, $C_{1-4}$ fluoroalkyl, $OR^6$, CN, $CO_2C_{1-4}$ alkyl, $N(R^6)_2$ and $NO_2$;

$R^5$ is hydrogen, $C(O)R^7$, $S(O)_2R^8$, $C_{3-7}$ cycloalkyl or $C_{1-4}$ alkyl optionally substituted by $OR^6$, $C_{3-7}$ cycloalkyl, aryl, heterocyclyl or heteroaryl, wherein the cyclic groups may be substituted with one or more substituents selected from halo, $C_{1-2}$ alkyl, $C_{1-2}$ fluoroalkyl, $OR^6$, CN, $N(R^6)_2$ and $NO_2$;

$R^6$ are independently hydrogen, $C_{1-4}$ alkyl, $C_{3-7}$ cycloalkyl, aryl, heterocyclyl or heteroaryl, wherein the cyclic groups may be substituted with one or more substituents selected from halo, $C_{1-4}$ alkyl, $C_{1-4}$ fluoroalkyl, $OR^9$, CN, $SO_2CH_3$, $N(R^{10})_2$ and $NO_2$; or a group $N(R^{10})_2$ may form a 4- to 7-membered heterocyclic ring optionally containing a further heteroatom selected from O and $NR^{10}$;

$R^7$ is hydrogen, $C_{1-4}$ alkyl, $OR^6$, $N(R^6)_2$, aryl or heteroaryl;
$R^8$ is $C_{1-4}$ alkyl, $C_{1-4}$ fluoroalkyl, aryl or heteroaryl;
$R^9$ is hydrogen, $C_{1-2}$ alkyl or $C_{1-2}$ fluoroalkyl;
$R^{10}$ is hydrogen or $C_{1-4}$ alkyl;
$R^{11}$ is phenyl; and
$R^{12}$ is hydrogen, $C_{1-4}$ alkyl or $C_{3-7}$ cycloalkyl;
provided that the compound is not:
a) tert-butyl 4-(3-pyridin-4-ylbenzyl)piperidine-1-carboxylate; or
b) 4-(3-pyridin-4-ylbenzyl)piperidine.

Examples of the group V include pyridinyl, pyridazinyl, pyrimidinyl, pyrazinyl and triazinyl.

In the compounds of formula (I) V may for example represent a 6-membered heteroaryl ring of the formula:

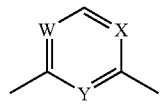

wherein one or two of W, X and Y are N and the others are CH.

Preferably the n groups of A and B do not both represent 0.
In A, n is preferably 0, 1 or 2, more preferably 0.
In B, n is preferably 2 or 3, more preferably 2.
When one of the $CH_2$ groups in B is replaced, it is preferably replaced by O, $NR^5$, $S(O)_m$ or C(O); more preferably it is replaced by O or $NR^5$.

$R^1$ is preferably 4-pyridyl optionally substituted by 1 or 2 halo, $C_{1-4}$ alkyl, $C_{1-4}$ fluoroalkyl, $C_{2-4}$ alkenyl, $C_{2-4}$ alkynyl, $C_{3-7}$ cycloalkyl, aryl, $OR^6$, CN, $NO_2$, $S(O)_mR^6$, $CON(R^6)_2$, $N(R^6)_2$, $NR^{10}COR^6$, $NR^{10}SO_2R^6$, $SO_2N(R^6)$, 4- to 7-membered heterocyclyl or 5- or 6-membered heteroaryl groups; more preferably 4-pyridyl optionally substituted by halo, $C_{1-4}$ alkyl, $C_{1-4}$ alkoxy or CN; even more preferably 4-pyridyl, optionally substituted by halo, $C_{1-4}$ alkyl or CN; and especially 4-pyridyl, optionally substituted by CN.

When $R^2$ is a 4- to 7-membered heterocyclyl, containing one or two nitrogen atoms it is preferably substituted, the substitution is preferably on the nitrogen atom.

$R^2$ is preferably a 4- to 7-membered cycloalkyl substituted by $R^3$ or $C(O)OR^3$, especially $R^3$, or a 4- to 7-membered heterocyclyl containing one nitrogen atom which is substituted by $C(O)OR^4$ or a 6-membered nitrogen containing heteroaryl group, more preferably a 4- to 7-membered heterocyclyl containing one nitrogen atom which is substituted by $C(O)OR^4$.

$R^2$ is more preferably a 4- to 7-membered cycloalkyl substituted by $R^3$, or a 4- to 7-membered heterocyclyl containing one nitrogen atom which is substituted by $C(O)OR^4$.

A particularly preferred $R^2$ group is piperidinyl, especially 4-piperidinyl, which is substituted on the nitrogen atom by $C(O)OR^4$.

$R^3$ is preferably $C_{3-8}$ alkyl which may contain a $CH_2$ group that may be replaced by O, or $C_{3-7}$ cycloalkyl, more preferably $R^3$ is $C_{3-8}$ alkyl.

$R^4$ is preferably $C_{2-8}$ alkyl, $C_{2-8}$ alkenyl or $C_{2-8}$ alkynyl, any of which may be optionally substituted with up to 5 fluoro or chloro atoms, and may contain a $CH_2$ group that may be replaced by O, or $C_{3-7}$ cycloalkyl, aryl, 5- to 6-membered heteroaryl containing one or two nitrogen atoms, $C_{1-4}$ alkyl$C_{3-7}$ cycloalkyl or $C_{1-4}$ alkylaryl, any of which may be substituted with one or more substituents selected from halo, $C_{1-4}$ alkyl, $C_{1-4}$ fluoroalkyl, $OR^6$ and $CO_2C_{1-4}$ alkyl.

More preferably $R^4$ is $C_{3-6}$ alkyl optionally substituted with up to 5 fluoro or chloro atoms, e.g. 3 fluoro or chloro atoms, and which may contain a $CH_2$ group that may be replaced by O, or $C_{3-7}$ cycloalkyl.

$R^5$ is preferably hydrogen or $C_{1-4}$ alkyl, more preferably $C_{1-4}$ alkyl.

$R^6$ is preferably hydrogen, $C_{1-4}$ alkyl or $C_{3-7}$ cycloalkyl, more preferably $C_{1-4}$ alkyl.

$R^7$ is preferably hydrogen or $C_{1-4}$ alkyl.

$R^8$ is preferably $C_{1-4}$ alkyl or $C_{1-4}$ fluoroalkyl.

A specific group of compounds of the invention which may be mentioned are those of formula (Ia), or a pharmaceutically acceptable salt thereof:

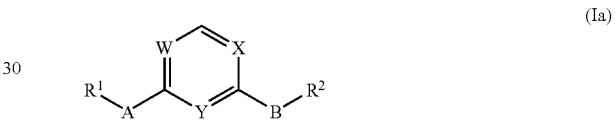

(Ia)

wherein one or two of W, X and Y are N and the others are CH;

A is $(CH_2)_n$;
B is $(CH_2)_n$, where one of the $CH_2$ groups may be replaced by O, $NR^6$, S(O), or C(O);
n is independently 0, 1, 2 or 3;
m is 0, 1 or 2;
$R^1$ is 3- or 4-pyridyl or 4-pyrimidinyl any of which may be optionally substituted by one or more substituents selected from halo, $C_{1-4}$ alkyl, $C_{1-4}$ fluoroalkyl, $C_{3-7}$ cycloalkyl, $OR^5$, CN, $NO_2$, $N(R^6)_2$, $CON(R^6)_2$ or a 5- or 6-membered heteroaryl group;
$R^2$ is 4- to 7-membered cycloalkyl substituted by $R^3$, C(O)$OR^3$, $C(O)R^3$ or $S(O)_2R^3$, or 4 to 7-membered heterocyclyl, containing one or two nitrogen atoms, which is unsubstituted or substituted by $C(O)OR^4$, $C(O)R^3$ or $S(O)_2R^3$;
$R^3$ is $C_{3-7}$ alkyl, $C_{3-7}$ alkenyl or $C_{3-7}$ alkynyl any of which may contain a $CH_2$ group that may be replaced by O, or $C_{3-7}$ cycloalkyl, aryl or $C_{1-4}$ alkylaryl, wherein the aryl groups may be substituted with one or more substituents selected from halo, $C_{1-4}$ alkyl, $C_{1-4}$ fluoroalkyl, $OR^5$, CN, $N(R^6)_2$ and $NO_2$;
$R^4$ is $C_{2-7}$ alkyl, $C_{2-7}$ alkenyl or $C_{2-7}$ alkynyl any of which may contain a $CH_2$ group that may be replaced by O, or $C_{3-7}$ cycloalkyl, aryl or $C_{1-4}$ alkylaryl, wherein the aryl groups may be substituted with one or more substituents selected from halo, $C_{1-4}$ alkyl, $C_{1-4}$ fluoroalkyl, $OR^6$, CN, $N(R^6)_2$ and $NO_2$;
$R^5$ are independently hydrogen, $C_{1-4}$ alkyl or $C_{1-4}$ fluoroalkyl; and
$R^6$ are independently hydrogen and $C_{1-4}$ alkyl.

A preferred group of compounds of the invention are the compounds of formula (Ib), and pharmaceutically acceptable salts thereof:

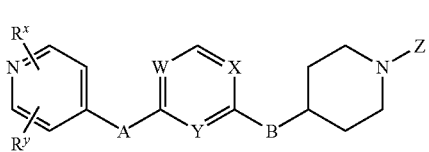

(Ib)

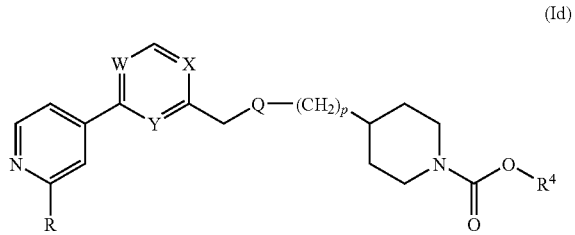

(Id)

wherein one or two of W, X and Y are N and the others are CH;

A is —CH=CH— or $(CH_2)_n$;

B is —CH=CH— or $(CH_2)_n$, where one of the $CH_2$ groups may be replaced by O, $NR^5$, $S(O)_m$ or C(O);

n is independently 0, 1, 2 or 3, provided that not both n are 0;

m is independently 0, 1 or 2;

$R^x$ and $R^y$ are independently selected from hydrogen, halo, $C_{1-4}$ alkyl, $C_{1-4}$ fluoroalkyl, $C_{2-4}$ alkenyl, $C_{2-4}$ alkynyl, $C_{3-7}$ cycloalkyl, aryl, $OR^6$, CN, $NO_2$, $S(O)R^6$, $CON(R^6)_2$, $N(R^6)_2$, $NR^{10}COR^6$, $NR^{10}SO_2R^6$, $SO_2N(R^6)_2$, a 4- to 7-membered heterocyclyl group and a 5- or 6-membered heteroaryl group;

Z is $C(O)OR^4$, $C(O)R^3$, $S(O)_2R^3$, $C(O)NHR^4$ or a 5- or 6-membered nitrogen containing heteroaryl group;

$R^3$ is $C_{3-4}$ alkyl, $C_{3-4}$ alkenyl or $C_{3-8}$ alkynyl, any of which may be optionally substituted with up to 5 fluoro or chloro atoms, and may contain a $CH_2$ group that may be replaced by O, or $C_{3-7}$ cycloalkyl, aryl, heterocyclyl, heteroaryl, $C_{1-4}$ alkyl$C_{3-7}$ cycloalkyl, $C_{1-4}$ alkylaryl, $C_{1-4}$ alkylheterocyclyl or $C_{1-4}$ alkylheteroaryl, any of which may be optionally substituted with one or more substituents selected from halo, $C_{1-4}$ alkyl, $C_{1-4}$ fluoroalkyl, $OR^6$, CN, $CO_2C_{1-4}$ alkyl, $N(R^6)_2$ and $NO_2$;

$R^4$ is $C_{2-8}$ alkyl, $C_{2-8}$ alkenyl or $C_{2-8}$ alkynyl, any of which may be optionally substituted with up to 5 fluoro or chloro atoms, and may contain a $CH_2$ group that may be replaced by O, or $C_{3-7}$ cycloalkyl, aryl, heterocyclyl, heteroaryl, $C_{1-4}$ alkyl$C_{3-7}$ cycloalkyl, $C_{1-4}$ alkylaryl, $C_{1-4}$ alkylheterocyclyl or $C_{1-4}$ alkylheteroaryl, any of which may be substituted with one or more substituents selected from halo, $C_{1-4}$ alkyl, $C_{1-4}$ fluoroalkyl, $OR^6$, CN, $CO_2C_{1-4}$ alkyl, $N(R^6)_2$ and $NO_2$;

$R^6$ are independently hydrogen, or $C_{1-4}$ alkyl, $C_{3-7}$ cycloalkyl, aryl, heterocyclyl or heteroaryl, wherein the cyclic groups may be substituted with one or more substituents selected from halo, $C_{1-4}$ alkyl, $C_{1-4}$ fluoroalkyl, $OR^9$, CN, $SO_2CH_3$, $N(R^{10})_2$ and $NO_2$; or a group $N(R^{10})_2$ may form a 4- to 7-membered heterocyclic ring optionally containing a further heteroatom selected from O and $NR^{10}$;

$R^9$ is hydrogen, $C_{1-2}$ alkyl or $C_{1-2}$ fluoroalkyl; and $R^{10}$ is hydrogen or $C_{1-4}$ alkyl.

A further preferred group of compounds of the invention are the compounds of formula (Ic), and pharmaceutically acceptable salts thereof:

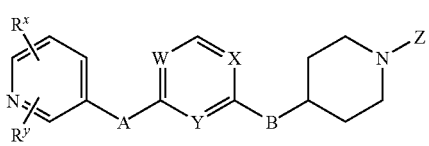

(Ic)

wherein W, X, Y, Z, A, B, $R^x$ and $R^y$ are as defined for formula (Ib).

A further preferred group of compounds of the invention are the compounds of formula (Id), and pharmaceutically acceptable salts thereof:

wherein one or two of W, X and Y are N and the others are CH;

Q is O, $NR^5$ or $CH_2$;

R is hydrogen, halo, $C_{1-4}$ alkyl, $C_{1-4}$ fluoroalkyl, $C_{2-4}$ alkenyl, $C_{2-4}$ alynyl, $C_{3-7}$ cycloalkyl, aryl, $OR^6$, CN, $NO_2$, $S(O)_mR^6$, $CON(R^6)_2$, $N(R^6)_2$, $NR^{10}COR^6$, $NR^{10}SO_2R^6$, $SO_2N(R^6)_2$, a 4- to 7-membered heterocyclyl group or a 5- or 6-membered heteroaryl group;

$R^4$ is $C_{2-8}$ alkyl, $C_{2-8}$ alkenyl or $C_{2-8}$ alkynyl, any of which may be optionally substituted with up to 5 fluoro or chloro atoms, and contain a $CH_2$ group that may be replaced by O, or $C_{3-7}$ cycloalkyl, aryl, heterocyclyl, heteroaryl, $C_{1-4}$ alkyl$C_{3-7}$ cycloalkyl, $C_{1-4}$ alkylaryl, $C_{1-4}$ alkylheterocyclyl or $C_{1-4}$ alkylheteroaryl, any of which may be substituted with one or more substituents selected from halo, $C_{1-4}$ alkyl, $C_{1-4}$ fluoroalkyl, $OR^6$, CN, $CO_2C_{1-4}$ alkyl, $N(R^6)_2$ and $NO_2$;

$R^5$ is $C_{1-4}$ alkyl;

$R^6$ are independently hydrogen, or $C_{1-4}$ alkyl, $C_{3-7}$ cycloalkyl, aryl, heterocyclyl or heteroaryl, wherein the cyclic groups may be substituted with one or more substituents selected from halo, $C_{1-4}$ alkyl, $C_{1-4}$ fluoroalkyl, $OR^9$, CN, $SO_2CH_3$, $N(R^{10})_2$ and $NO_2$; or a group $N(R^{10})_2$ may form a 4- to 7-membered heterocyclic ring optionally containing a further heteroatom selected from O and $NR^{10}$;

$R^9$ is hydrogen, $C_{1-2}$ alkyl or $C_{1-2}$ fluoroalkyl;

$R^{10}$ is hydrogen or $C_{1-4}$ alkyl; and p is 0 or 1.

In the compounds of formula (Id) R is preferably hydrogen, halo, $C_{1-4}$ alkyl, $C_{1-4}$ alkoxy or CN.

While the preferred groups for each variable have generally been listed above separately for each variable, preferred compounds of this invention include those in which several or each variable in formula (I) is selected from the preferred, more preferred or particularly listed groups for each variable. Therefore, this invention is intended to include all combinations of preferred, more preferred and particularly listed groups. The preferences listed above also apply, where applicable, to the compounds of formula (Ia) to (Id).

Specific compounds of the invention which may be mentioned are those included in the Examples and pharmaceutically acceptable salts thereof.

As used herein, unless stated otherwise, "alkyl" as well as other groups having the prefix "alk" such as, for example, alkenyl, alkynyl, and the like, means carbon chains which may be linear or branched or combinations thereof. Examples of alkyl groups include methyl, ethyl, propyl, isopropyl, butyl, sec- and tert-butyl, pentyl, hexyl, heptyl and the like. "Alkenyl", "alkynyl" and other like terms include carbon chains having at least one unsaturated carbon-carbon bond.

The term "fluoroalkyl" includes alkyl groups substituted by one or more fluorine atoms, e.g. $CH_2F$, $CHF_2$ and $CF_3$.

The term "cycloalkyl" means carbocycles containing no heteroatoms, and includes monocyclic and bicyclic saturated and partially saturated carbocycles. Examples of cycloalkyl include cyclopropyl, cyclobutyl, cyclopentyl, cyclohexyl and cycloheptyl. Examples of partially saturated cycloalkyl groups include cyclohexene and indane. Cycloalkyl groups will typically contain 3 to 10 ring carbon atoms in total (e.g. 3 to 6, or 8 to 10).

The term "halo" includes fluorine, chlorine, bromine, and iodine atoms.

The term "aryl" includes phenyl and naphthyl, in particular phenyl.

Unless otherwise indicated the term "heterocyclyl" and "heterocyclic ring" includes 4- to 10-membered monocyclic and bicyclic saturated rings, e.g. 4- to 7-membered monocyclic saturated rings, containing up to three heteroatoms selected from N, O and S. Examples of heterocyclic rings include oxetane, tetrahydrofuran, tetrahydropyran, oxepane, oxocane, thietane, tetrahydrothiophene, tetrahydrothiopyran, thiepane, thiocane, azetidine, pyrrolidine, piperidine, azepane, azocane, [1,3]dioxane, oxazolidine, piperazine, and the like. Other examples of heterocyclic rings include the oxidised forms of the sulfur-containing rings. Thus, tetrahydrothiophene 1-oxide, tetrahydrothiophene 1,1-dioxide, tetrahydrothiopyran 1-oxide, and tetrahydrothiopyran 1,1-dioxide are also considered to be heterocyclic rings.

Unless otherwise stated, the term "heteroaryl" includes mono- and bicyclic 5- to 10-membered, e.g. monocyclic 5- or 6-membered, heteroaryl rings containing up to 4 heteroatoms selected from N, O and S. Examples of such heteroaryl rings are furyl, thienyl, pyrrolyl, pyrazolyl, imidazolyl, oxazolyl, isoxazolyl, thiazolyl, isothiazolyl, triazolyl, oxadiazolyl, thiadiazolyl, tetrazolyl, pyridinyl, pyridazinyl, pyrimidinyl, pyrazinyl and triazinyl. Bicyclic heteroaryl groups include bicyclic heteroaromatic groups where a 5- or 6-membered heteroaryl ring is fused to a phenyl or another heteroaromatic group. Examples of such bicyclic heteroaromatic rings are benzofuran, benzothiophene, indole, benzoxazole, benzothiazole, indazole, benzimidazole, benzotriazole, quinoline, isoquinoline, quinazoline, quinoxaline and purine.

Compounds described herein may contain one or more asymmetric centers and may thus give rise to diastereomers and optical isomers. The present invention includes all such possible diastereomers as well as their racemic mixtures, their substantially pure resolved enantiomers, all possible geometric isomers, and pharmaceutically acceptable salts thereof. The above formula (I) is shown without a definitive stereochemistry at certain positions. The present invention includes all stereoisomers of formula (I) and pharmaceutically acceptable salts thereof. Further, mixtures of stereoisomers as well as isolated specific stereoisomers are also included. During the course of the synthetic procedures used to prepare such compounds, or in using racemization or epimerization procedures known to those skilled in the art, the products of such procedures can be a mixture of stereoisomers.

When a tautomer of the compound of formula (I) exists, the present invention includes any possible tautomers and pharmaceutically acceptable salts thereof, and mixtures thereof, except where specifically drawn or stated otherwise.

When the compound of formula (I) and pharmaceutically acceptable salts thereof exist in the form of solvates or polymorphic forms, the present invention includes any possible solvates and polymorphic forms. A type of a solvent that forms the solvate is not particularly limited so long as the solvent is pharmacologically acceptable. For example, water, ethanol, propanol, acetone or the like can be used.

The term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (ic and ous), ferric, ferrous, lithium, magnesium, potassium, sodium, zinc and the like salts. Particularly preferred are the ammonium, calcium, magnesium, potassium and sodium salts. Salts derived from pharmaceutically acceptable organic non-toxic bases include salts of primary, secondary, and tertiary amines, as well as cyclic amines and substituted amines such as naturally occurring and synthesized substituted amines. Other pharmaceutically acceptable organic non-toxic bases from which salts can be formed include arginine, betaine, caffeine, choline, N',N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

When the compound of the present invention is basic, its corresponding salt can be conveniently prepared from pharmaceutically acceptable non-toxic acids, including inorganic and organic acids. Such acids include, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like Since the compounds of formula (I) are intended for pharmaceutical use they are preferably provided in substantially pure form, for example at least 60% pure, more suitably at least 75% pure, especially at least 98% pure (% are on a weight for weight basis).

The compounds of formula (I) can be prepared as described below, in which $R^1$, $R^2$, A, B and V are as defined above.

Compounds of formula (I) wherein B represents —$CH_2$—$NR^5$—B'— can be prepared as shown in Scheme 1 by reaction of a compound of formula (II) with an amine of formula (III) under reductive amination conditions known to those skilled in the art, e.g. using dichloromethane as solvent and sodium triacetoxyborohydride as reducing agent.

Scheme 1

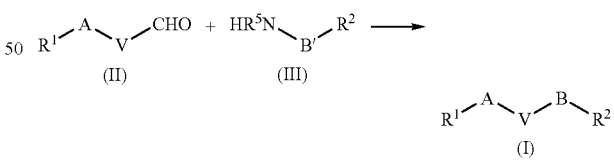

Compounds of formula (II) may be prepared by oxidation of a compound of formula (IV), using e.g. selenium dioxide in a suitable solvent such as dioxane at elevated temperature:

Amines of formula (III) are either commercially available or may be prepared by techniques known to those skilled in the art.

Compounds of formula (IV) where V is pyrimidine may be prepared as shown in Scheme 2 by reaction of a compound of formula (V) with e.g. acetylacetaldehyde dimethylacetate and a base such as DBU in a solvent such as DMF at elevated temperature:

Scheme 2

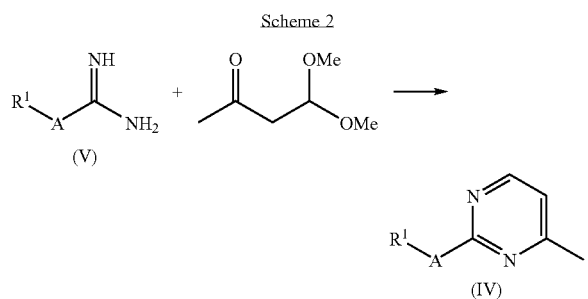

(IV)

Compounds of formula (I) wherein V represents a nitrogen containing heterocycle having a N atom adjacent to the point of attachment of group —B—$R^2$ may be prepared by reaction of a compound of formula (VI) wherein X represents halo, e.g. bromo, with an amine of formula (III) in a solvent such as DMF in the presence of a base e.g. DIPEA:

(VI)

Compounds of formula (I) may also be prepared as shown in Scheme 3 by reaction of a boronic acid ester of formula (VI) and a compound of formula (VIII) wherein X is halo e.g. bromo using an appropriate catalysts such as palladium (tetrakis)triphenylphosphine in a suitable solvent such as toluene in the presence of a base e.g. sodium carbonate:

Scheme 3

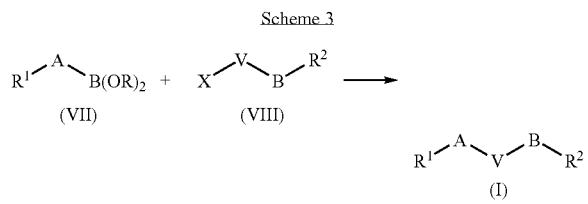

Compounds of formula (I) in which $R^2$ contains either a carbamate or a sulfonamide group may be synthesised as described in Scheme 4. Compounds of formula (IX), in which P represents a suitable protecting group, for example tert-butoxycarbonyl (Boc), may be synthesised as outlined above. The protecting group is firstly removed under suitable conditions to afford compounds of formula (X). In the case of the Boc group this can be achieved by treatment of compounds of formula (IX) with a suitable acid, such as trifluoroacetic acid, in an appropriate solvent, such as $CH_2Cl_2$. Treatment of compounds of formula (X) with chloroformates of formula (XI), which are generally commercially available or can be readily synthesised, in a suitable solvent, such as $CH_2Cl_2$, in the presence of a suitable base, such as triethylamine, affords compounds of formula (I). Similarly, compounds of formula (X) may be reacted with sulfonyl chlorides of formula (XII), which are generally commercially available or can be readily synthesised, in a suitable solvent, such as $CH_2Cl_2$, in the presence of a suitable base, such as triethylarine, to afford compounds of formula (I). Compounds of formula (I) in which $R^2$ contains a urea moiety may be prepared by reacting a compound of formula (X) with an isocyanate of formula O=C=N—$R^4$. Furthermore, compounds of formula (I) in which $R^2$ is 4-7-membered heterocyclyl substituted with a heteroaryl group may be prepared by reacting the amine (X) with the appropriate heteroaryl chloride or bromide under Pd(0) catalysis in the presence of a suitable ligand and base (Urgaonkar, S.; Hu, J.-H.; Verkade, J. G. *J. Org. Chem.* 2003, 68, 84168423).

Scheme 4

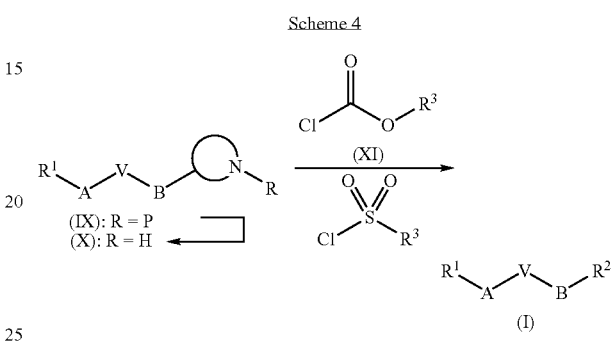

Compounds of formula (I) in which $R^2$ contains an amide group may be synthesised from compounds of formula (X) and a suitable acid ($R^3$COOH), or activated derivative thereof, in an amide bond forming reaction.

Compounds of formula (I) where $R^2$ contains an ester moiety may be synthesised as illustrated in Scheme 5. Compounds of formula (XIII) in which R is an alkyl group, for example a methyl group, may be synthesised using procedures described above. The alkyl group is firstly removed under appropriate conditions to afford compounds of formula (XIV). For example, when R=Me compounds of formula (XIII) may be generated in the presence of a suitable base, for example LiOH, in a suitable solvent, such as water-methanol. The acids of formula (XIV) are then condensed with alcohols of formula (XV), which are commercially available or can be synthesised using known techniques. The condensation may be achieved by, for example, heating compounds of formula (XIV) with alcohols of formula (XV) in the presence of thionyl chloride, giving rise to compounds of formula (I).

Scheme 5

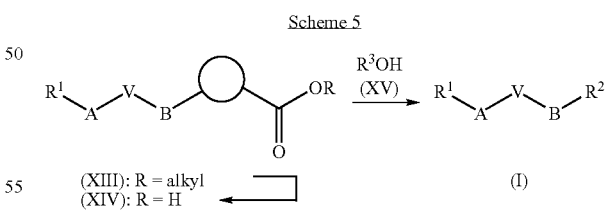

Compounds of formula (I) where $R^3$ contains an ether group may also be synthesised from compounds of formula (XIII) as illustrated in Scheme 6. Compounds of formula (XIII) may be converted to the corresponding alcohol (XVI) by the action of a suitable reducing agent, for example diisobutylaluminium hydride, in a suitable solvent, such as $CH_2Cl_2$ and can then be treated firstly with a suitable base, such as sodium hydride, in a suitable solvent, such as THF, followed by an appropriate alkylating agent, such as an alkyl halide of formula (XVII) to afford compounds of formula (I).

Scheme 6

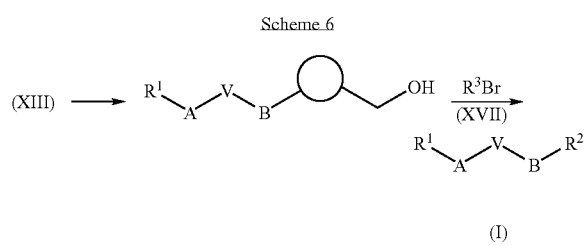

(I)

Compounds of formula (I) where B contains a $NR^5$ group where $R^5$ is hydrogen can be further transformed into compounds of formula (I) where $R^5$ is $C(O)R^7$, $S(O)_2R^8$, or an optionally substituted $C_{1-4}$ alkyl group using standard techniques known to those with skill in the art for acylation, sulfonylation and reductive amination respectively.

Compounds of the formula (I) where $R^1$ is pyridyl optionally substituted with CN can be prepared from the corresponding unsubstituted pyridine by the Reissert reaction (Fife, W. K. *J. Org. Chem.* 1983, 48, 1375-1377). Similar reactions can be used to prepare the compounds where $R^1$ is pyridyl optionally substituted with halogen (Walters, M. A.; Shay, J. J. *Tetrahedron Lett.* 1995, 36, 7575-7578). The compounds where $R^1$ is pyridyl optionally substituted with halogen can be transformed into the corresponding compounds where $R^1$ is pyridyl optionally substituted with $C_{1-4}$ alkyl by transition metal-catalysed cross-coupling reactions (Fürstner, A., et al. *J. Am. Chem. Soc.* 2002, 124, 13856-13863).

Other compounds of formula (I) may be prepared by methods analogous to those described above or by methods known per se.

Further details for the preparation of the compounds of formula (I) are found in the examples.

The compounds of formula (I) may be prepared singly or as compound libraries comprising at least 2, for example 5 to 1,000, compounds and more preferably 10 to 100 compounds of formula (I). Compound libraries may be prepared by a combinatorial "split and mix" approach or by multiple parallel synthesis using either solution or solid phase chemistry, using procedures known to those skilled in the art.

During the synthesis of the compounds of formula (I), labile functional groups in the intermediate compounds, e.g. hydroxy, carboxy and amino groups, may be protected. The protecting groups may be removed at any stage in the synthesis of the compounds of formula (I) or may be present on the final compound of formula (I). A comprehensive discussion of the ways in which various labile functional groups may be protected and methods for cleaving the resulting protected derivatives is given in, for example, Protective Groups in Organic Chemistry, T. W. Greene and P. G. M. Wuts, (1991) Wiley-Interscience, New York, $2^{nd}$ edition.

Any novel intermediates as defined above are also included within the scope of the invention.

As indicated above the compounds of formula (I) are useful as GPR116 agonists, e.g. for the treatment and/or prophylaxis of obesity and diabetes. For such use the compounds of formula (I) will generally be administered in the form of a pharmaceutical composition.

The invention also provides a compound of formula (I), including the compounds of provisos a) and b), or a pharmaceutically acceptable salt thereof, for use as a pharmaceutical.

The invention also provides a pharmaceutical composition comprising a compound of formula (I), including the compounds of provisos a) and b), in combination with a pharmaceutically acceptable carrier.

Preferably the composition is comprised of a pharmaceutically acceptable carrier and a non-toxic therapeutically effective amount of a compound of formula (I), including the compounds of provisos a) and b), or a pharmaceutically acceptable salt thereof.

Moreover, the invention also provides a pharmaceutical composition for the treatment of disease by modulating GPR116, resulting in the prophylactic or therapeutic treatment of obesity, e.g. by regulating satiety, or for the treatment of diabetes, comprising a pharmaceutically acceptable carrier and a non-toxic therapeutically effective amount of compound of formula (I), including the compounds of provisos a) and b), or a pharmaceutically acceptable salt thereof.

The pharmaceutical compositions may optionally comprise other therapeutic ingredients or adjuvants. The compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions may be conveniently presented in unit dosage form and prepared by any of the methods well known in the art of pharmacy.

In practice, the compounds of formula (I), or pharmaceutically acceptable salts thereof, can be combined as the active ingredient in intimate admixture with a pharmaceutical carrier according to conventional pharmaceutical compounding techniques. The carrier may take a wide variety of forms depending on the form of preparation desired for administration, e.g. oral or parenteral (including intravenous).

Thus, the pharmaceutical compositions can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion, or as a water-in-oil liquid emulsion. In addition to the common dosage forms set out above, the compound of formula (I), or a pharmaceutically acceptable salt thereof, may also be administered by controlled release means and/or delivery devices. The compositions may be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

The compounds of formula (I), including the compounds of provisos a) and b), or pharmaceutically acceptable salts thereof, can also be included in pharmaceutical compositions in combination with one or more other therapeutically active compounds.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media may be employed. For example, water, glycols, oils, alcohols, flavoring agents, preservatives, coloring agents, and the like may be used to form oral liquid preparations such as suspensions, elixirs and solutions; while carriers such as starches, sugars, microcrystalline cellulose, diluents, granulating agents, lubricants, binders, disintegrating agents, and the like may be used to form oral solid preparations such as powders, capsules and tablets. Because of their ease of administration, tablets and capsules are the preferred oral dosage units whereby solid pharmaceutical carriers are employed. Optionally, tablets may be coated by standard aqueous or nonaqueous techniques.

A tablet containing the composition of this invention may be prepared by compression or molding, optionally with one or more accessory ingredients or adjuvants. Compressed tablets may be prepared by compressing, in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Each tablet preferably contains from about 0.05 mg to about 5 g of the active ingredient and each cachet or capsule preferably containing from about 0.05 mg to about 5 g of the active ingredient.

For example, a formulation intended for the oral administration to humans may contain from about 0.5 mg to about 5 g of active agent, compounded with an appropriate and convenient amount of carrier material which may vary from about 5 to about 95 percent of the total composition. Unit dosage forms will generally contain between from about 1 mg to about 2 g of the active ingredient, typically 25 mg, 50 mg, 100 mg, 200 mg, 300 mg, 400 mg, 500 mg, 600 mg, 800 mg, or 1000 mg.

Pharmaceutical compositions of the present invention suitable for parenteral administration may be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), vegetable oils, and suitable mixtures thereof.

Pharmaceutical compositions of the present invention can be in a form suitable for topical use such as, for example, an aerosol, cream, ointment, lotion, dusting powder, or the like. Further, the compositions can be in a form suitable for use in transdermal devices. These formulations may be prepared, using a compound of formula (I), or a pharmaceutically acceptable salt thereof, via conventional processing methods. As an example, a cream or ointment is prepared by admixing hydrophilic material and water, together with about 5 wt % to about 10 wt % of the compound, to produce a cream or ointment having a desired consistency.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories may be conveniently formed by first admixing the composition with the softened or melted carrier(s) followed by chilling and shaping in molds.

In addition to the aforementioned carrier ingredients, the pharmaceutical formulations described above may include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient. Compositions containing a compound of formula (I), or pharmaceutically acceptable salts thereof, may also be prepared in powder or liquid concentrate form.

Generally, dosage levels on the order of 0.01 mg/kg to about 150 mg/kg of body weight per day are useful in the treatment of the above-indicated conditions, or alternatively about 0.5 mg to about 7 g per patient per day. For example, obesity may be effectively treated by the administration of from about 0.01 to 50 mg of the compound per kilogram of body weight per day, or alternatively about 0.5 mg to about 3.5 g per patient per day.

It is understood, however, that the specific dose level for any particular patient will depend upon a variety of factors including the age, body weight, general health, sex, diet, time of administration, route of administration, rate of excretion, drug combination and the severity of the particular disease undergoing therapy.

The compounds of formula (I), including the compounds of provisos a) and b), and pharmaceutically acceptable salts thereof, may be used in the treatment of diseases or conditions in which GPR116 plays a role.

Thus the invention also provides a method for the treatment of a disease or condition in which GPR116 plays a role comprising a step of administering to a subject in need thereof an effective amount of a compound of formula (I), including the compounds of provisos a) and b), or a pharmaceutically acceptable salt thereof.

Diseases or conditions in which GPR116 plays a role include obesity and diabetes. In the context of the present application the treatment of obesity is intended to encompass the treatment of diseases or conditions such as obesity and other eating disorders associated with excessive food intake e.g. by reduction of appetite and body weight, maintenance of weight reduction and prevention of rebound and diabetes (including Type 1 and Type 2 diabetes, impaired glucose tolerance, insulin resistance and diabetic complications such as neuropathy, nephropathy, retinopathy, cataracts, cardiovascular complications and dyslipidaemia). And the treatment of patients who have an abnormal sensitivity to ingested fats leading to functional dyspepsia. The compounds of the invention may also be used for treating metabolic diseases such as metabolic syndrome (syndrome X), impaired glucose tolerance, hyperlipidemia, hypertriglyceridemia, hypercholesterolemia, low HDL levels and hypertension.

The invention also provides a method for the regulation of satiety comprising a step of administering to a subject in need thereof an effective amount of a compound of formula (I), including the compounds of provisos a) and b), or a pharmaceutically acceptable salt thereof.

The invention also provides a method for the treatment of obesity comprising a step of administering to a subject in need thereof an effective amount of a compound of formula (I), including the compounds of provisos a) and b), or a pharmaceutically acceptable salt thereof.

The invention also provides a method for the treatment of diabetes, including Type 1 and Type 2 diabetes, particularly type 2 diabetes, comprising a step of administering to a patient in need thereof an effective amount of a compound of formula (I), including the compounds of provisos a) and b), or a pharmaceutically acceptable salt thereof.

The invention also provides a method for the treatment of metabolic syndrome (syndrome X), impaired glucose tolerance, hyperlipidemia, hypertriglyceridemia, hypercholesterolemia, low HDL levels or hypertension comprising a step of administering to a patient in need thereof an effective amount of a compound of formula (I), including the compounds of provisos a) and b), or a pharmaceutically acceptable salt thereof.

The invention also provides a compound of formula (I), including the compounds of provisos a) and b), or a pharmaceutically acceptable salt thereof, for use in the treatment of a condition as defined above.

The invention also provides the use of a compound of formula (I), including the compounds of provisos a) and b), or a pharmaceutically acceptable salt thereof, in the manufacture of a medicament for the treatment of a condition as defined above.

In the methods of the invention the term "treatment" includes both therapeutic and prophylactic treatment.

The compounds of formula (I), including the compounds of provisos a) and b), or pharmaceutically acceptable salts thereof, may be administered alone or in combination with one or more other therapeutically active compounds. The other therapeutically active compounds may be for the treatment of the same disease or condition as the compounds of formula (I) or a different disease or condition. The therapeutically active compounds may be administered simultaneously, sequentially or separately.

The compounds of formula (I) may be administered with other active compounds for the treatment of obesity and/or diabetes, for example insulin and insulin analogs, gastric lipase inhibitors, pancreatic lipase inhibitors, sulfonyl ureas and analogs, biguanides, α2 agonists, glitazones, PPAR-γ agonists, mixed PPAR-α/γ agonists, RXR agonists, fatty acid oxidation inhibitors, α-glucosidase inhibitors, β-agonists, phosphodiesterase inhibitors, lipid lowering agents, glycogen phosphorylase inhibitors, antiobesity agents e.g. pancreatic lipase inhibitors, MCH-1 antagonists and CB-1 antagonists (or inverse agonists), amylin antagonists, lipoxygenase inhibitors, somostatin analogs, glucokinase activators, glucagon antagonists, insulin signalling agonists, PTP1B inhibitors, gluconeogenesis inhibitors, antilypolitic agents, GSK inhibitors, galanin receptor agonists, anorectic agents, CCK receptor agonists, leptin, serotonergic/dopaminergic antiobesity drugs, reuptake inhibitors e.g. sibutramine, CRF antagonists, CRF binding proteins, thyromimetic compounds, aldose reductase inhibitors, glucocorticoid receptor antagonists, NHE-1 inhibitors or sorbitol dehydrogenase inhibitors.

Combination therapy comprising the administration of a compound of formula (I), or a pharmaceutically acceptable salt thereof, and at least one other antiobesity agent represents a further aspect of the invention.

The present invention also provides a method for the treatment of obesity in a mammal, such as a human, which method comprises administering an effective amount of a compound of formula (I), including the compounds of provisos a) and b), or a pharmaceutically acceptable salt thereof, and another antiobesity agent, to a mammal in need thereof.

The invention also provides the use of a compound of formula (I), including the compounds of provisos a) and b), or a pharmaceutically acceptable salt thereof, and another antiobesity agent for the treatment of obesity.

The invention also provides the use of a compound of formula (I), including the compounds of provisos a) and b), or a pharmaceutically acceptable salt thereof, in the manufacture of a medicament for use in combination with another antiobesity agent, for the treatment of obesity.

The compound of formula (I), including the compounds of provisos a) and b), or a pharmaceutically acceptable salt thereof, and the other antiobesity agent(s) may be co-administered or administered sequentially or separately.

Co-administration includes administration of a formulation which includes both the compound of formula (I), including the compounds of provisos a) and b), or a pharmaceutically acceptable salt thereof, and the other antiobesity agent(s), or the simultaneous or separate administration of different formulations of each agent. Where the pharmacological profiles of the compound of formula (I), or a pharmaceutically acceptable salt thereof, and the other antiobesity agent(s) allow it, coadministration of the two agents may be preferred.

The invention also provides the use of a compound of formula (I), including the compounds of provisos a) and b), or a pharmaceutically acceptable salt thereof, and another antiobesity agent in the manufacture of a medicament for the treatment of obesity.

The invention also provides a pharmaceutical composition comprising a compound of formula (I), including the compounds of provisos a) and b), or a pharmaceutically acceptable salt thereof, and another antiobesity agent, and a pharmaceutically acceptable carrier. The invention also encompasses the use of such compositions in the methods described above.

GPR116 agonists are of particular use in combination with centrally acting antiobesity agents.

The other antiobesity agent for use in the combination therapies according to this aspect of the invention is preferably a CB-1 modulator, e.g. a CB-1 antagonist or inverse agonist. Examples of CB-1 modulators include SR141716 (rimonabant) and SLV-319 ((4S)-(−)-3-(4-chlorophenyl)-N-methyl-N-[(4-chlorophenyl)sulfonyl]-4-phenyl-4,5-dihydro-1H-pyrazole-1-carboxamide); as well as those compounds disclosed in EP576357, EP656354, WO 03/018060, WO 03/020217, WO 03/020314, WO 03/026647, WO 03/026648, WO 03/027076, WO 03/040105, WO 03/051850, WO 03/051851, WO 03/053431, WO 03/063781, WO 03/075660, WO 03/077847, WO 03/078413, WO 03/082190, WO 03/082191, WO 03/082833, WO 03/084930, WO 03/084943, WO 03/086288, WO 03/087037, WO 03/088968, WO 04/012671, WO 04/013120, WO 04/026301, WO 04/029204, WO 04/034968, WO 04/035566, WO 04/037823 WO 04/052864, WO 04/058145, WO 04/058255, WO 04/060870, WO 04/060888, WO 04/069837, WO 04/069837, WO 04/072076, WO 04/072077, WO 04/078261 and WO 04/108728, and the references disclosed therein.

Other diseases or conditions in which GPR116 has been suggested to play a role include those described in WO 00/50562 and U.S. Pat. No. 6,468,756, for example cardiovascular disorders, hypertension, respiratory disorders, gestational abnormalities, gastrointestinal disorders, immune disorders, musculoskeletal disorders, depression, phobias, anxiety, mood disorders and Alzheimer's disease.

All publications, including, but not limited to, patents and patent application cited in this specification, are herein incorporated by reference as if each individual publication were specifically and individually indicated to be incorporated by reference herein as fully set forth.

The invention will now be described by reference to the following examples which are for illustrative purposes and are not to be construed as a limitation of the scope of the present invention.

EXAMPLES

Materials and Methods

Column chromatography was carried out on $SiO_2$ (40-63 mesh) unless specified otherwise. LCMS data were obtained as follows: Atlantis 3μ $C_{18}$ column (3.0×20.0 mm, flow rate=0.85 mL/min) eluting with a $H_2O$—$CH_3CN$ solution containing 0.1% $HCO_2H$ over 6 min with UV detection at 220 nm. Gradient information: 0.0-4.3 min 100% $H_2O$; 0.3-4.25 min: Ramp up to 10% $H_2O$-90% $CH_3CN$; 4.25-4.4 min: Ramp up to 100% $CH_3CN$; 4.4-4.9 min: Hold at 100% $CH_3CN$; 4.9-6.0 min: Return to 100% $H_2O$. The mass spectra were obtained using an electrospray ionisation source in either the positive ($ES^+$) or negative ($ES^-$) ion modes.

$^1H$ NMR spectra were recorded on a Varian Mercury 400 spectrometer at 400 MHz.

Abbreviations and acronyms: Ac: Acetyl; DBU: 1,8-Diazabicyclo[5.4.0]undec-7-ene; DCE: 1,2-Dichloroethane; DIPEA: N,N-Diisopropylethylamine; DMF: N,N-Dimethylformamide; Et: Ethyl; Me: Methyl; RT: Retention time; rt: Room temperature; THF: Tetrahydrofuran.

The syntheses of the following compounds have been reported previously: 4-methylaminomethyl-piperidine-1-carboxylic acid tert-butyl ester: Hiscock, S. D., et al. WO 03/049737; 2-pyridin-4-yl-pyrimidin-4-ol: Medwid, J. B., et al. *J. Med. Chem.* 1990, 33, 1230-1241.

Preparation 1: 4-Bromo-2-pyridin-4-yl-pyrimidine

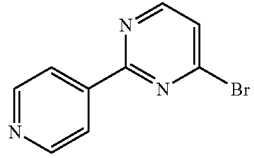

2-Pyridin-4-yl-pyrimidin-4-ol (200 mg, 1.16 mmol) was suspended in DCE (10 mL) then $POBr_3$ (497 mg, 1.73 mmol) was added in one portion. The reaction mixture was heated to 95° C. (bath) for 18 h then cooled to 20° C. $H_2O$ (30 mL) and $CH_2Cl_2$ (30 mL) were added, then the biphasic mixture was stirred vigorously for 30 min. The layers were separated and the aqueous phase was extracted with $CH_2Cl_2$ (3×30 mL). The combined organics were evaporated to dryness to afford the title compound: m/z ($ES^+$)=236, 238 (1:1) $[M+H]^+$.

Preparation 2:
2-Pyridin-4-yl-pyrimidine-4-carbaldehyde

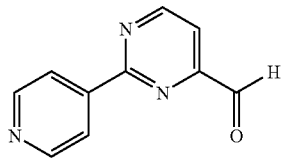

Isonicotinamidine hydrochloride (5.00 g, 31.7 mmol) and acetaldehyde dimethylacetal (8.44 mL, 63.5 mmol) were combined and heated to 110° C. in anhydrous DMF (35 mL) in the presence of DBU (14.20 mL, 95.2 mmol) for 3 h. The reaction mixture was cooled to 20° C., then stirred for 16 h, before being concentrated in vacuo. The residue was partitioned between $H_2O$ (100 mL) and EtOAc (100 mL). The aqueous layer was extracted with EtOAc (2×50 mL), then the combined organics were washed with brine (50 mL), dried ($MgSO_4$), filtered and concentrated under reduced pressure. Flash column chromatography (EtOAc) of the residue gave 4-methyl-2-pyridin-4-yl-pyrimidine: $δ_H$ $((CD_3)_2SO)$: 2.57 (3H, s), 7.45 (1H, d), 8.21-8.26 (2H, m), 8.72-8.77 (2H, m), 8.82 (1H, d). To a solution of this compound (1.06 g, 6.17 mmol) in anhydrous dioxane (20 mL) was added $SeO_2$ (2.05 g, 18.51 mol), then the mixture was heated to reflux for 90 h. The reaction mixture was cooled to 20° C. then filtered, washing with EtOAc. The filtrate was evaporated to dryness, then the residue was suspended in $CH_2Cl_2$. The suspension was filtered, washing with $CH_2Cl_2$, then the filtrate was evaporated to dryness to furnish the title compound: $δ_H$ $(CDCl_3)$: 7.80 (1H, d), 8.38 (2H, d), 8.83 (2H, d), 9.13 (1H, d), 10.15 (1H, s).

Preparation 3:
(6-Bromopyridin-2-ylmethyl)methylamine

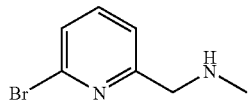

To a solution of 6-bromopyridine-2-carbaldehyde (1.00 g, 5.38 mmol) in $CH_2Cl_2$ (20 mL) was added methylamine (4.04 mL, 2M/THF, 8.08 mmol) then to the stirred solution was added sodium triacetoxyborohydride (1.37 g, 6.46 mmol). After stirring at rt for 18 h, the mixture was partitioned between saturated aqueous $NaHCO_3$ (50 mL) and $CH_2Cl_2$ (100 mL). The layers were separated then the aqueous extracted with $CH_2Cl_2$ (2×30 mL). The combined organics were washed with brine (50 mL), dried ($MgSO_4$), filtered and concentrated in vacuo. Purification via flash column chromatography (5% $MeOH/CH_2Cl_2$) afforded the desired compound: $δ_H$ $(CDCl_3)$: 2.49 (3H, s), 3.86 (2H, s), 7.31 (1H, d), 7.38 (1H, d), 7.53 (1H, t).

Preparation 4: [(6-Bromopyridin-2-ylmethyl)methylamino]methyl}piperidine-1-carboxylic acid tert-butyl ester

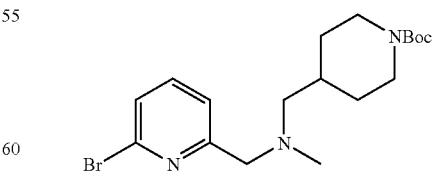

To a solution of (6-bromo-pyridin-2-ylmethyl)methylamine (Preparation 3, 100 mg, 0.50 mmol) in $CH_2Cl_2$ (5 mL) was added 4-formylpiperidine-1-carboxylic acid tert-butyl ester (117 mg, 0.55 mmol) then sodium triacetoxyborohydride (116 mg, 0.55 mmol). The reaction mixture was stirred for 16 h at rt then partitioned between saturated aqueous NaHCO$_3$ (30 mL) and CH$_2$Cl$_2$ (30 mL). The layers were separated and the aqueous extracted with CH$_2$Cl$_2$ (2×20 mL). The combined organics were washed with brine (30 mL), dried (MgSO$_4$), filtered and concentrated in vacuo. Purification via flash column chromatography (CH$_2$Cl$_2$ to 2% MeOH/CH$_2$Cl$_2$) furnished the desired compound: δ$_H$ (CDCl$_3$): 0.95-1.08 (2H, m), 1.44 (9H, s), 1.54-1.69 (1H, m), 1.75 (2H, d), 2.21-2.26 (5H, m), 2.67 (2H, t), 3.61 (2H, s), 3.98-4.15 (2H, m), 7.33 (1H, d), 7.44 (1H, d), 7.51 (1H, t).

Example 1

4-{[Methyl-(2-pyridin-4-ylpyrimidin-4-yl)-amino]methyl}piperidine-1-carboxylic acid tert-butyl ester

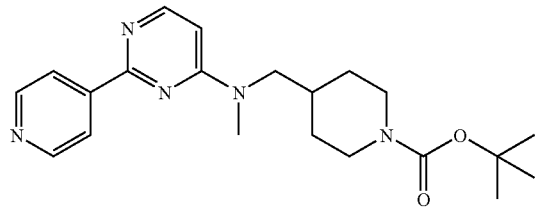

To a solution of 4-methylaminomethylpiperidine-1-carboxylic acid tert-butyl ester (41 mg, 0.18 mmol) in anhydrous DMF (3 mL) was added 4-bromo-2-pyridin-4-yl-pyrimidine (Preparation 1, 42 mg, 0.18 mmol) and DIPEA (63 μL, 0.36 mmol), then the resulting solution was heated to 86° C. (bath) for 6 h. The reaction mixture was cooled to 20° C., then H$_2$O (20 mL) and EtOAc (10 mL) were added. The layers were separated then the aqueous phase was extracted with EtOAc (2×30 mL). The combined organics were washed with brine (30 mL), dried (MgSO$_4$), filtered and concentrated in vacuo. Flash column chromatography (EtOAc) gave the title compound: RT=2.87 nm in; m/z (ES$^+$)=384 [M+H]$^+$.

Example 2

4-{[Methyl-(2-pyridin-4-ylpyrimidin-4-ylmethyl)amino]methyl}piperidine-1-carboxylic acid tert-butyl ester

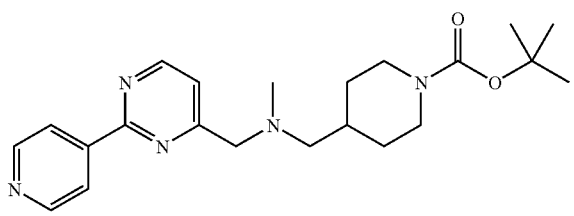

To a solution of 4-methylaminomethylpiperidine-1-carboxylic acid tert-butyl ester (37 mg, 0.16 mmol) in anhydrous CH$_2$Cl$_2$ (3 mL) was added 2-pyridin-4-yl-pyrimidine-4-carbaldehyde (Preparation 2, 30 mg, 0.16 mmol) followed by NaBH(OAc)$_3$ (38 mg, 0.18 mmol). The mixture was stirred vigorously at rt for 24 h, before being partitioned between CH$_2$Cl$_2$ (30 mL) and H$_2$O (20 mL). The aqueous phase was extracted with CH$_2$Cl$_2$ (20 mL), then the combined organics were washed with brine (20 mL), dried (MgSO$_4$) and filtered and concentrated in vacuo. Flash column chromatography (EtOAc) gave the title compound. RT=2.36 min; m/z (ES$^+$)= 398 [M+H]$^+$.

Example 3

4-[([2,4']Bipyridinyl-6-ylmethylmethylamino)methyl]piperidine-1-carboxylic acid tert-butyl ester

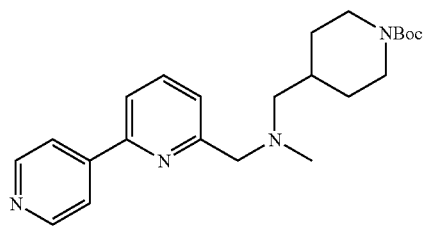

To a solution of 4-{[[(6-bromopyridin-2-ylmethyl)methylamino]methyl}piperidine-1-carboxylic acid tert-butyl ester (Preparation 4, 88 mg, 0.28 mmol) in toluene (5 mL, anhydrous) was added palladium tetrakis(triphenylphosphine) (13 mg, 0.01 mmol) and sodium carbonate (53 mg in 1.5 mL water, deoxygenated). To the vigorously stirred biphasic mixture was added 4-(4,4,5,5-tetramethyl-[1,3,2]dioxaborolan-2-yl)pyridine 57 mg, 0.28 mmol) and the reaction mixture heated to 86° C. (bath) for 3 days. The reaction mixture was allowed to cool to rt then aqueous ammonia (2M, 15 mL) was added with vigorous stirring. After 10 min, ethyl acetate (30 mL) was added and the layers separated. The aqueous was extracted with ethyl acetate (2×20 mL) and the combined organics washed with brine (20 mL), dried (MgSO$_4$), filtered and concentrated in vacuo. Purification via flash chromatography (5% MeOH/CH$_2$Cl$_2$) afforded the title compound: δ$_H$ (CDCl$_3$): 0.96-1.12 (2H, m), 1.43 (9H, s), 1.63-1.73 (1H, m), 1.78 (2H, d), 2.26-2.32 (5H, m), 2.69 (2H, t), 3.72 (2H, s), 4.00-4.14 (2H, m), 7.51 (1H, d), 7.65 (1H, d), 7.77 (1H, t), 7.88 (2H, d), 8.69 (2H, d). RT=2.38 min; m/z (ES$^+$)=397 [M+H]$^+$.

The biological activity of the compounds of the invention may be tested in the following assay systems:

Yeast Reporter Assay

The yeast cell-based reporter assays have previously been described in the literature (e.g. see Miret J. J. et al, 2002, J. Biol. Chem., 277:6881-6887; Campbell R. M. et al, 1999, Bioorg. Med. Chem. Lett., 9:2413-2418; King K. et al, 1990, Science, 250:121-123); WO 99/14344; WO 00/12704; and U.S. Pat. No. 6,100,042). Briefly, yeast cells have been engineered such that the endogenous yeast G-alpha (GPA1) has been deleted and replaced with G-protein chimeras constructed using multiple techniques. Additionally, the endogenous yeast alpha-cell GPCR, Ste3 has been deleted to allow for a homologous expression of a mammalian GPCR of choice. In the yeast, elements of the pheromone signaling transduction pathway, which are conserved in eukaryotic cells (for example, the mitogen-activated protein kinase pathway), drive the expression of Fus1. By placing β-galactosidase (LacZ) under the control of the Fus1 promoter (Fus1p), a system has been developed whereby receptor activation leads to an enzymatic read-out.

Yeast cells were transformed by an adaptation of the lithium acetate method described by Agatep et al, (Agatep, R. et al, 1998, Transformation of *Saccharomyces cerevisiae* by the lithium acetate/single-stranded carrier DNA/polyethylene glycol (LiAc/ss-DNA/PEG) protocol. Technical Tips Online, Trends Journals, Elsevier). Briefly, yeast cells were grown overnight on yeast tryptone plates (YT). Carrier single-stranded DNA (101 g), 2 µg of each of two Fus1p-LacZ reporter plasmids (one with URA selection marker and one with TRP), 2 µg of GPR116 (human or mouse receptor) in yeast expression vector (2 kg origin of replication) and a lithium acetate/polyethylene glycol/TE buffer was pipetted into an Eppendorf tube. The yeast expression plasmid containing the receptor/no receptor control has a LEU marker. Yeast cells were inoculated into this mixture and the reaction proceeds at 30° C. for 60 min. The yeast cells were then heat-shocked at 42° C. for 15 min. The cells were then washed and spread on selection plates. The selection plates are synthetic defined yeast media minus LEU, URA and TRP (SD-LUT). After incubating at 30° C. for 2-3 days, colonies that grow on the selection plates were then tested in the LacZ assay.

In order to perform fluorimetric enzyme assays for β-galactosidase, yeast cells carrying the human or mouse GPR116 receptor were grown overnight in liquid SD-LUT medium to an unsaturated concentration (i.e. the cells were still dividing and had not yet reached stationary phase). They were diluted in fresh medium to an optimal assay concentration and 90 µl of yeast cells are added to 96-well black polystyrene plates (Costar). Compounds, dissolved in DMSO and diluted in a 10% DMSO solution to 10× concentration, were added to the plates and the plates placed at 30° C. for 4 h. After 4 h, the substrate for the β-galactosidase was added to each well. In these experiments, Fluorescein di(β-D-galactopyranoside) was used (FDG), a substrate for the enzyme that releases fluorescein, allowing a fluorimetric read-out. 20 µl per well of 500 µM FDG/2.5% Triton X100 was added (the detergent was necessary to render the cells permeable). After incubation of the cells with the substrate for 60 min, 20 µl per well of 1M sodium carbonate was added to terminate the reaction and enhance the fluorescent signal. The plates were then read in a fluorimeter at 485/535 nm.

Compounds of the invention gave an increase in fluorescent signal of at least ~1.5-fold that of the background signal (i.e. the signal obtained in the presence of 1% DMSO without compound).

cAMP Assay

A stable cell line expressing recombinant human GPR116 was established and this cell line was used to investigate the effect of compounds of the invention on intracellular levels of cyclic AMP (cAMP). The cells monolayers were washed with phosphate buffered saline and stimulated at 37° C. for 30 min with various concentrations of compound in stimulation buffer plus 1% DMSO. Cells were then lysed and cAMP content determined using the Perkin Elmer AlphaScreen™ (Amplified Luminescent Proximity Homogeneous Assay) cAMP kit. Buffers and assay conditions were as described in the manufacturer's protocol.

Compounds of the invention showed a concentration-dependant increase in intracellular cAMP level.

In Vivo Feeding Study

The effect of compounds of the invention on body weight and food and water intake may be examined in freely-feeding male Sprague-Dawley rats maintained on reverse-phase lighting. Test compounds and reference compounds are dosed by appropriate routes of administration (e.g. intraperitoneally or orally) and measurements made over the following 24 h. Rats are individually housed in polypropylene cages with metal grid floors at a temperature of 21±4° C. and 55±20% humidity. Polypropylene trays with cage pads are placed beneath each cage to detect any food spillage. Animals are maintained on a reverse phase light-dark cycle (lights off for 8 h from 09.30-17.30 h) during which time the room was illuminated by red light. Animals have free access to a standard powdered rat diet and tap water during a two week acclimatization period. The diet is contained in glass feeding jars with aluminum lids. Each lid has a 3-4 cm hole in it to allow access to the food. Animals, feeding jars and water bottles are weighed (to the nearest 0.1 g) at the onset of the dark period. The feeding jars and water bottles are subsequently measured 1, 2, 4, 6 and 24 h after animals are dosed with a compound of the invention and any significant differences between the treatment groups at baseline compared to vehicle-treated controls.

Anti-Diabetic Effects of Compounds of the Invention in an In-Vitro Model of Pancreatic Beta Cells (HIT-T15)

Cell Culture

HIT-T15 cells (passage 60) may be obtained from ATCC, and cultured in RPMI1640 medium supplemented with 10% fetal calf serum and 30 nM sodium selenite. AU experiments should be performed with cells at less than passage 70, in accordance with the literature, which describes altered properties of this cell line at passage numbers above 81 (Zhang H J, Walseth T F, Robertson R P. Insulin secretion and cAMP metabolism in HIT cells. Reciprocal and serial passage-dependent relationships. *Diabetes*. 1989 January; 38(1):44-8).

cAMP Assay

HIT-T15 cells are plated in standard culture medium in 96-well plates at 100,000 cells/0.1 ml/well and cultured for 24 hr and the medium then discarded. Cells are incubated for 15 min at room temperature with 100 µl stimulation buffer (Hanks buffered salt solution, 5 mM HEPES, 0.5 mM IBMX, 0.1% BSA, pH 7.4). This is discarded and replaced with compound dilutions over the range 0.001, 0.003, 0.01, 0.03, 0.1, 0.3, 1, 3, 10, 30 µM in stimulation buffer in the presence of 0.5% DMSO. Cells are incubated at room temperature for 30 min. Then 75 µl lysis buffer (5 mM HEPES, 0.3% Tween-20, 0.1% BSA, pH 7.4) added per well and the plate shaken at 900 rpm for 20 min. Particulate matter is removed by centrifugation at 300 rpm for 5 min, then the samples are transferred in duplicate to 384-well plates, and processed following the Perkin Elmer AlphaScreen cAMP assay kit instructions. Briefly 25 µl reactions are set up containing 8 µl sample, 5 µl acceptor bead mix and 12 µl detection mix, such that the concentration of the final reaction components is the same as stated in the kit instructions. Reactions are incubated at room temperature for 150 min, and the plate read using a Packard Fusion instrument. Measurements for cAMP are compared to a standard curve of known cAMP amounts (0.01, 0.03, 0.1, 0.3, 1, 3, 10, 30, 100, 300, 1000 nM) to convert the readings to absolute cAMP amounts. Data was analysed using XLfit 3 software.

Insulin Secretion Assay

HIT-T15 cells are plated in standard culture medium in 12-well plates at 106 cells/1 ml/well and cultured for 3 days and the medium then discarded. Cells are washed ×2 with supplemented Krebs-Ringer buffer (KRB) containing 119 mM NaCl, 4.74 mM KCl, 2.54 mM $CaCl_2$, 1.19 mM $MgSO_4$, 1.19 mM $KH_2PO_4$, 25 mM $NaHCO_3$, 10 mM HEPES at pH 7.4 and 0.1% bovine serum albumin. Cells are incubated with 1 ml KRB at 37° C. for 30 min which is then discarded. This is followed by a second incubation with KRB for 30 min, which is collected and used to measure basal insulin secretion levels for each well. Compound dilutions (0, 0.1, 0.3, 1, 3, 10 uM) are then added to duplicate wells in 1 ml KRB, supplemented with 5.6 mM glucose. After 30 min incubation at 37° C. samples are removed for determination of insulin levels. Measurement of insulin is done using the Mercodia Rat insulin ELISA kit, following the manufacturers instructions, with a standard curve of known insulin concentrations. For each well insulin levels are subtracted by the basal secretion level from the pre-incubation in the absence of glucose. Data is analysed using XLfit 3 software.

What is claimed is:

1. A compound of the formula (Ib), or a pharmaceutically acceptable salt thereof:

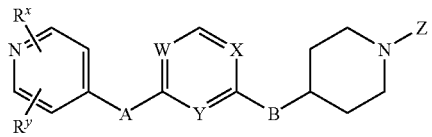

(Ib)

wherein one or two of W, X and Y are N and the others are CH;

A is —CH=CH— or $(CH_2)_n$;

B is —CH=CH— or $(CH_2)_n$, where one of the $CH_2$ groups may be replaced by O, $NR^5$, $S(O)_m$ or $C(O)$;

n is independently 0, 1, 2 or 3, provided that not both n are 0;

m is 0, 1 or 2;

$R^x$ and $R^y$ are each independently selected from hydrogen, halo, $C_{1-4}$ alkyl, $C_{1-4}$ fluoroalkyl, $C_{2-4}$ alkenyl, $C_{2-4}$ alkynyl, $C_{3-7}$ cycloalkyl, aryl, $OR^6$, CN, $NO_2$, $S(O)_mR^6$, $CON(R^6)_2$, $N(R^6)_2$, $NR^{10}COR^6$, $NR^{10}SO_2R^6$, $SO_2N(R^6)_2$, a 4- to 7-membered heterocyclyl group and a 5- or 6-membered heteroaryl group;

Z is $C(O)OR^4$, $C(O)R^3$, $S(O)_2R^3$, $C(O)NHR^4$ or a 5- or 6-membered nitrogen containing heteroaryl group;

$R^3$ is $C_{3-8}$ alkyl, $C_{3-8}$ alkenyl or $C_{3-8}$ alkynyl, any of which are optionally substituted with up to 5 fluoro or chloro atoms, and may contain a $CH_2$ group that may be replaced by O, or $C_{3-7}$ cycloalkyl, aryl, heterocyclyl, heteroaryl, $C_{1-4}$alkyl$C_{3-7}$ cycloalkyl, $C_{1-4}$ alkylaryl, $C_{1-4}$ alkylheterocyclyl or $C_{1-4}$ alkylheteroaryl, any of which are optionally substituted with one or more substituents selected from halo, $C_{1-4}$ alkyl, $C_{1-4}$ fluoroalkyl, $OR^6$, CN, $CO_2C_{1-4}$ alkyl, $N(R^6)_2$ and $NO_2$;

$R^4$ is $C_{2-8}$ alkyl, $C_{2-8}$ alkenyl or $C_{2-8}$ alkynyl, any of which are optionally substituted with up to 5 fluoro or chloro atoms, and may contain a $CH_2$ group that may be replaced by O, or $C_{3-7}$ cycloalkyl, aryl, heterocyclyl, heteroaryl, $C_{1-4}$alkyl$C_{3-7}$ cycloalkyl, $C_{1-4}$ alkylaryl, $C_{1-4}$ alkylheterocyclyl or $C_{1-4}$ alkylheteroaryl, any of which may be substituted with one or more substituents selected from halo, $C_{1-4}$ alkyl, $C_{1-4}$ fluoroalkyl, $OR^6$, CN, $CO_2C_{1-4}$ alkyl, $N(R^6)_2$ and $NO_2$;

$R^5$ is hydrogen, $C(O)R^7$, $S(O)_2R^8$, $C_{3-7}$ cycloalkyl or $C_{1-4}$ alkyl optionally substituted by $OR^6$, $C_{3-7}$ cycloalkyl, aryl, heterocyclyl or heteroaryl, wherein the cyclic groups may be substituted with one or more substituents selected from halo, $C_{1-2}$ alkyl, $C_{1-2}$ fluoroalkyl, $OR^6$, CN, $N(R^6)_2$ and $NO_2$;

$R^6$ is independently hydrogen, or $C_{1-4}$ alkyl, $C_{3-7}$ cycloalkyl, aryl, heterocyclyl or heteroaryl, wherein the cyclic groups may be substituted with one or more substituents selected from halo, $C_{1-4}$ alkyl, $C_{1-4}$ fluoroalkyl, $OR^9$, CN, $SO_2CH_3$, $N(R^{10})_2$ and $NO_2$; or a group $N(R^{10})_2$ may form a 4- to 7-membered heterocyclic ring optionally containing a further heteroatom selected from O and $NR^{10}$;

$R^7$ is hydrogen, $C_{1-4}$alkyl, $OR^6$, $N(R^6)_2$, aryl or heteroaryl;

$R^8$ is $C_{1-4}$alkyl, $C_{1-4}$fluoroalkyl, aryl or heteroaryl;

$R^9$ is hydrogen, $C_{1-2}$ alkyl or $C_{1-2}$ fluoroalkyl; and $R^{10}$ is hydrogen or $C_{1-4}$ alkyl.

2. A compound according to claim 1 having the formula (Id), or a pharmaceutically acceptable salt thereof:

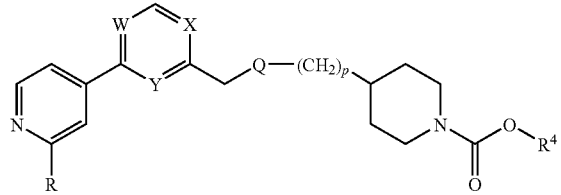

(Id)

wherein one or two of W, X and Y are N and the others are CH;

Q is O, $NR^5$ or $CH_2$;

R is hydrogen, halo, $C_{1-4}$ alkyl, $C_{1-4}$ fluoroalkyl, $C_{2-4}$ alkenyl, $C_{2-4}$ alkynyl, $C_{3-7}$ cycloalkyl, aryl, $OR^6$, CN, $NO_2$, $S(O)_mR^6$, $CON(R^6)_2$, $N(R^6)_2$, $NR^{10}COR^6$, $NR^{10}SO_2R^6$, $SO_2N(R^6)_2$, a 4- to 7-membered heterocyclyl group or a 5- or 6-membered heteroaryl group;

$R^4$ is $C_{2-8}$ alkyl, $C_{2-8}$ alkenyl or $C_{2-8}$ alkynyl, any of which are optionally substituted with up to 5 fluoro or chloro atoms, and contain a $CH_2$ group that may be replaced by O, or $C_{3-7}$ cycloalkyl, aryl, heterocyclyl, heteroaryl, $C_{1-4}$alkyl$C_{3-7}$ cycloalkyl, $C_{1-4}$ alkylaryl, $C_{1-4}$ alkylheterocyclyl or $C_{1-4}$ alkylheteroaryl, any of which may be substituted with one or more substituents selected from halo, $C_{1-4}$ alkyl, $C_{1-4}$ fluoroalkyl, $OR^6$, CN, $CO_2C_{1-4}$ alkyl, $N(R^6)_2$ and $NO_2$;

$R^5$ is $C_{1-4}$ alkyl;

$R^6$ is independently hydrogen, $C_{1-4}$ alkyl, $C_{3-7}$ cycloalkyl, aryl, heterocyclyl or heteroaryl, wherein the cyclic groups may be substituted with one or more substituents selected from halo, $C_{1-4}$ alkyl, $C_{1-4}$ fluoroalkyl, $OR^9$, CN, $SO_2CH_3$, $N(R^{10})_2$ and $NO_2$; or a group $N(R^{10})_2$ may form a 4- to 7-membered heterocyclic ring optionally containing a further heteroatom selected from O and $NR^{10}$;

$R^9$ is hydrogen, $C_{1-2}$ alkyl or $C_{1-2}$ fluoroalkyl;

$R^{10}$ is hydrogen or $C_{1-4}$ alkyl; and p is 0 or 1.

3. The compound of claim 1, wherein W and Y are N, and X is CH.

4. The compound of claim 1, wherein W and X are CH, and Y is N.

5. The compound of claim 1, wherein $R^4$ is $C_{2-8}$ alkyl.

6. The compound of claim 5, wherein $R^4$ is tert-butyl.

7. The compound of claim 1, wherein $R^x$ and $R^y$ are each independently hydrogen, halo, $C_{1-4}$ alkyl, $C_{1-4}$ alkoxy or CN.

8. The compound of claim 7, wherein $R^x$ is hydrogen.

9. The compound of claim 7, wherein $R^y$ is hydrogen.

10. The compound of claim 2, wherein Q is $NR^5$.

11. The compound of claim 10, wherein $R^5$ is methyl.

12. The compound of claim 2, wherein p is 1.

13. A pharmaceutical composition comprising a compound according to claim 1, or a pharmaceutically acceptable salt thereof and a pharmaceutically acceptable carrier.

14. A compound of formula (I) selected from:

4-{[Methyl-(2-pyridin-4-ylpyrimidin-4-yl)-amino] methyl}piperidine-1-carboxylic acid tert-butyl ester;

4-{[Methyl-(2-pyridin-4-ylpyrimidin-4-ylmethyl)amino]methyl}piperidine-1-carboxylic acid tert-butyl ester; and 4-[([2,4']Bipyridinyl-6-ylmethylmethylamino)methyl]piperidine-1-carboxylic acid tert-butyl ester;

or a pharmaceutically acceptable salt of any one thereof.

15. A method for the regulation of satiety comprising a step of administering to a subject in need thereof an effective amount of a compound according to claim 1, or a pharmaceutically acceptable salt thereof.

16. A method for the treatment of obesity comprising a step of administering to an obese subject an effective amount of a compound according to claim 1, or a pharmaceutically acceptable salt thereof.

17. A method for the treatment of Type 2 diabetes comprising a step of administering to a subject having Type 2 diabetes an effective amount of a compound according to claim 1, or a pharmaceutically acceptable salt thereof.

* * * * *